United States Patent
Quadling et al.

(10) Patent No.: US 8,532,355 B2
(45) Date of Patent: Sep. 10, 2013

(54) LIGHTING COMPENSATED DYNAMIC TEXTURE MAPPING OF 3-D MODELS

(75) Inventors: Mark Quadling, Plano, TX (US); Andrei Tchouprakov, Plano, TX (US); Gary Severance, Dallas, TX (US); Glen Freeman, Trophy Club, TX (US)

(73) Assignee: D4D Technologies, LLC, Richardson, TX (US)

( * ) Notice: Subject to any disclaimer, the term of this patent is extended or adjusted under 35 U.S.C. 154(b) by 16 days.

(21) Appl. No.: 13/427,497

(22) Filed: Mar. 22, 2012

(65) Prior Publication Data

US 2012/0236117 A1  Sep. 20, 2012

Related U.S. Application Data

(63) Continuation of application No. 12/266,942, filed on Nov. 7, 2008, now Pat. No. 8,144,954.

(60) Provisional application No. 60/986,580, filed on Nov. 8, 2007.

(51) Int. Cl.
   *G06K 9/00* (2006.01)
(52) U.S. Cl.
   USPC ............................................. 382/128
(58) Field of Classification Search
   USPC ................ 382/128, 154, 182, 183; 600/476; 356/602, 603
   See application file for complete search history.

(56) References Cited

U.S. PATENT DOCUMENTS

| | | |
|---|---|---|
| 6,281,904 B1 | 8/2001 | Reinhardt et al. |
| 6,744,923 B1 | 6/2004 | Zabih et al. |
| 7,142,312 B2 | 11/2006 | Quadling et al. |
| 7,184,150 B2 | 2/2007 | Quadling et al. |
| 7,226,338 B2 | 6/2007 | Duncan et al. |

(Continued)

OTHER PUBLICATIONS

Lempitsky, Victor; Seamless Mosaicing of Image Based Texture Maps, 16 pages.

(Continued)

*Primary Examiner* — Nathan Ha
(74) *Attorney, Agent, or Firm* — Haynes and Boone, LLP

(57) ABSTRACT

Methods, systems, and devices for generating textured 3D models are provided. The present disclosure describes methods, systems, and devices for combining multiple images onto a 3D model. In some instances, the textures of the images are applied to the 3D model dynamically so that the textured 3D model is viewable from different viewpoints in real time on a display. The present disclosure also describes methods, systems, and devices for selecting the images and, in particular, the portions of the selected images to map to defined portions of the 3D model. In addition, the present disclosure describes how to adjust the images themselves to remove the effects of directional lighting. Some aspects of the present disclosure are particularly useful in the context of a 3D modeling of dental preparations. In some instances, a 3D digitizer is used to produce 3D models of dental preparations.

19 Claims, 14 Drawing Sheets

(56) References Cited

U.S. PATENT DOCUMENTS

| | | |
|---|---|---|
| 7,270,592 B2 | 9/2007 | Duncan et al. |
| 7,312,879 B2 | 12/2007 | Johnston |
| 7,342,668 B2 | 3/2008 | Quadling et al. |
| 7,355,721 B2 | 4/2008 | Quadling et al. |
| 2004/0145753 A1* | 7/2004 | Lim et al. ............ 356/602 |
| 2004/0152987 A1 | 8/2004 | Haisch |
| 2004/0249274 A1 | 12/2004 | Yaroslavsky et al. |
| 2005/0013477 A1* | 1/2005 | Ratti et al. ............ 382/154 |
| 2005/0143662 A1* | 6/2005 | Marchitto et al. ........ 600/473 |
| 2005/0254709 A1* | 11/2005 | Geshwind et al. ........ 382/182 |
| 2006/0036181 A1* | 2/2006 | Treado et al. ............ 600/476 |
| 2006/0183082 A1 | 8/2006 | Quadling et al. |

OTHER PUBLICATIONS

U.S. Appl. No. 10/906,390, filed Feb. 17, 2005, (now Publication No. 2006/0183082), published Aug. 17, 2006, Entitled: Method and Computer System for Creating Dental Restoration Model.

European Patent Office, Notification of Transmittal of the International Search Report and The Written Opinion of the International Searching Authority, or the Declaration for PCT/US2008/082774, mailed Aug. 31, 2009, 16 pages.

* cited by examiner

LIGHTING COMPENSATED DYNAMIC TEXTURE MAPPING OF 3-D MODELS

PRIORITY

The present application is a continuation of U.S. patent application Ser. No. 12/266,942, filed on Nov. 7, 2008, now U.S. Pat. No. 8,144,954, which claims priority to U.S. Provisional Patent Application No. 60/986,580 filed Nov. 8, 2007 and titled "Lighting Compensated Dynamic Texture Mapping of 3D Models," each of which is hereby incorporated by reference in its entirety.

BACKGROUND

The present disclosure relates to three-dimensional imaging and modeling of physical objects. In particular, the present disclosure relates to texture mapping three-dimensional models of physical objects. In some instances, the present disclosure relates to texture mapping of three-dimensional models representing one or more dental articles, such as molds, castings, dentition, prepared dentition, soft tissue (e.g., gums), and/or other dental articles.

Techniques have been developed to generate three-dimensional ("3D") models of physical objects. The 3D models are generated by a computer that processes data representing the surfaces and contours of the physical object. The data is generated by optically scanning the physical object and detecting or capturing the light reflected off of the object. Based on various processing techniques such as Moire, interferometry, triangulation, or otherwise the shape, surfaces, and/or contours of the object are modeled by the computer.

In some instances, a 3D digitizer is used to produce a 3D model of the physical object by observing the object from a number of different positions. Each position produces a cloud of 3D coordinates. The complete 3D model is generated from a superposition of the multiple 3D point clouds. A 3D model built in this manner contains only the coordinate information, and has no texture associated with it since the underlying data is in the form of collections of 3D coordinates only. In some instances an image of the object is taken from each different position. Each image is represented by a collection of pixels, usually arranged in a rectangular array. By correlating the pixels of the images to the 3D coordinates of the model, the images can be projected or mapped onto the 3D model to provide texture to the 3D model. The methods employed for such mappings perform an offline computation where all of the textures are merged or blended together onto the model. These methods—which are computationally expensive and slow—typically cannot be employed in real time 3D modeling situations where new images are being added to a 3D model as the 3D is built and the user expects to see the results immediately. Also, the merging and blending of the textures are designed to improve the appearance of the 3D model, which can result in an inaccurate depiction of the texture in the 3D model as compared to the actual physical object.

There are also a number of complications that arise when texture mapping a 3D model with several images or views. First, in some instances the images will overlap, in which case a choice must be made as to which part of which image should be mapped to a particular part of the 3D model. In addition, if a light source is attached to the digitizer, then in every image the lighting conditions are different, which can cause the same area of the object to have a different appearance or texture in the different images. Further, while illuminating the object from a single fixed point relative to the object may limit some of the effects of having different lighting conditions for the different positions, the resulting images may have shadows that detract from the realism of the model. Further still, in the context of dental imaging some imaging devices require powdering or coating of the treatment site with a contrast or reflective material, such as titanium dioxide, in order to obtain the reflections utilized in determining the 3D coordinates. The powdering or coating of the treatment site prevents acquisition of the actual texture and color of the treatment site during the 3D data acquisition, in addition to increasing or introducing errors in the 3D coordinate data caused by non-uniformity of the powder thickness.

Accordingly, there is a need for improved methods, systems, and devices for three-dimensional modeling of physical objects and, in particular, texture mapping three-dimensional models of dental articles.

SUMMARY

Methods, systems, and devices for generating, displaying, and using textured 3D models are provided.

The present disclosure provides a means for combining multiple images onto a 3D model. In one aspect, the textures of the images are applied to the 3D model dynamically so that the textured 3D model is viewable from different viewpoints in real time on a computer display. The present disclosure also describes a means for selecting the images and, in particular, the portions of the selected images to map to defined portions of the 3D model. In addition, the present disclosure describes how to adjust the images themselves to remove the effects of directional lighting. In some instances of the present disclosure, as additional scans or images of an objected are obtained (which may change a shape of the 3D model and/or add additional image textures of the model), the textured model is updated in real time. Aspects of the present disclosure are particularly useful in the context of a 3D digitizer used for scanning in the oral cavity. Using aspects of the present disclosure, the 3D digitizer is used to produce 3D models that are rendered on a display in real time and are fully 3D dimensional while accurately depicting the surface textures of the item(s) being digitized. For example, in the case of scanning a preparation, a 3D model suitable for the manufacturing of CAD/CAM restorations is generated with the different substances of the preparation easily identified. For example, in some instances texturing of the 3D models distinguish between enamel, dentin, artificial restoration materials, areas of decay, areas of discoloration, and/or other features/materials. The textured 3D models of the present disclosure also aid in the CAD/CAM process by improving the accuracy of the determination of certain features, such as the margin.

In one embodiment, a system comprises a 3D digitizer and a processing system in communication with the 3D digitizer. The 3D digitizer includes an attached light source. The 3D digitizer is configured to obtain a plurality of images of an object and generate data representative of a surface of the object. The processing system generates a textured 3D model of the object from the plurality of images and the data representative of the surface of the object obtained from the 3D digitizer. The processing system adjusts an intensity of the plurality of images using an intensity function that compensates for effects of the attached light source. The processing system also maps textures from the plurality of adjusted images to corresponding points in the 3D model such that each visible point in the 3D model corresponds to a texture from one of the plurality of images. In some instances, the light source of the 3D digitizer is a laser light source. In some instances, the 3D digitizer is sized for intra-oral use and configured for obtaining a plurality of images of dental structures. Further, in some embodiments the system further comprises a display for displaying the textured 3D model generated by the processing system. In that regard, the processing system generates the textured 3D model and the display displays the textured 3D model in approximately real time in some instances.

In some embodiments, the processing system determines which textures from the plurality of images to map to the corresponding points in the 3D model based on a current viewpoint of the 3D model. In one embodiment, the processing system determines which textures from the plurality of images to map to the corresponding points in the 3D model by ordering the plurality of images based on a relative proximity of the corresponding viewpoint of the image to the current viewpoint of the 3D model, determining which portions of the 3D model can be mapped using the image closest in proximity to the current viewpoint of the 3D model, and mapping those portions of the 3D model with the corresponding textures the image closest in proximity to the current viewpoint. In some embodiments, the processing system continues the mapping by determining which portions of the 3D model can be mapped using the image next closest in proximity to the current viewpoint of the 3D model and maps those portions of the 3D model with the corresponding textures the image next closest in proximity to the current viewpoint until all portions of the 3D model visible from the current viewpoint are textured.

In another embodiment, a method of generating a textured 3D model is provided. The method includes scanning a physical object with a 3D digitizer and attached light source from a plurality of viewpoints to obtain a 3D model and a plurality of images of the object. The method also includes adjusting an intensity of the plurality of images using an intensity function that compensates for effects of the attached light source. Finally, the method includes mapping textures from the plurality of images to corresponding points in the 3D model to generate a textured 3D model of the object. In that regard, each point in the 3D model corresponds to a texture from one of the plurality of images. In some instances, the mapping of textures from the plurality of images to the corresponding points in the 3D model is dependent on a viewpoint of the 3D model. In some instances, the physical object is a dental item.

In another embodiment, a method of applying textures to a 3D model is provided. The method comprises scanning a physical object with a 3D digitizer and attached light source from a plurality of viewpoints to obtain a 3D model and a plurality of images of the object. The method also includes rendering the 3D model on a display from a first viewpoint, where rendering the 3D model comprises mapping textures from the plurality of images to corresponding points in the 3D model to generate a textured 3D model of the object. The mapping of the textures from the plurality of images comprises ordering the plurality of images based on a relative proximity of the viewpoint of the image to the first viewpoint of the 3D model, and mapping the textures to the corresponding points in the 3D model using the images having the closest relative proximity to the first viewpoint. In some instances, textures from the images do not overlap. If textures from multiple images are available to map to a single corresponding point of the 3D model, then the image having the closest proximity to the first viewpoint is utilized in some instances.

In another embodiment, a method of calibrating a digitizer is provided. The method comprises: providing a 3D digitizer comprising an attached light source; imaging a planar surface of uniform color with the 3D digitizer from a plurality of distances to obtain a plurality of images; determining an intensity map for each of the plurality of images; and determining an intensity function by interpolating between the intensity maps of the plurality of images, the intensity function compensating for effects caused by the attached light source. In some instances, the method further comprises imaging an object with the 3D digitizer to obtain a plurality of object images and adjusting each of the plurality of object images using the determined intensity function to compensate for effects caused by the attached light source. In some instances, the method further comprises generating a textured 3D model of the object based on the plurality of adjusted object images.

In some instances, the methods, systems, and devices of the present disclosure are utilized in designing and or manufacturing custom medical prosthetics. For example, in one aspect, a method of designing a dental prosthetic is provided. The method comprises scanning a dental preparation with a 3D digitizer from a plurality of viewpoints to obtain 3D coordinate data and a plurality of images and viewing, from a first viewpoint, a textured 3D model of the dental preparation generated from the 3D coordinate data and at least some of the plurality of images. The textures from at least some of plurality of images are applied to the surfaces of the 3D model visible in the first viewpoint based on a relative proximity of the viewpoint of an image to the first viewpoint of the 3D model. The method also comprises identifying and marking a first portion of a margin on the textured 3D model from the first viewpoint. The first portion of the margin is identified at least partially based on the textures of the surfaces of the 3D model. Additional portions of the margin are identified from other viewpoints in some instances. The method also comprises designing a dental prosthetic device based on the identified and marked margin.

Additional aspects, features, and embodiments of the present disclosure are described in the following detailed description.

DETAILED DESCRIPTION

Figure 1:
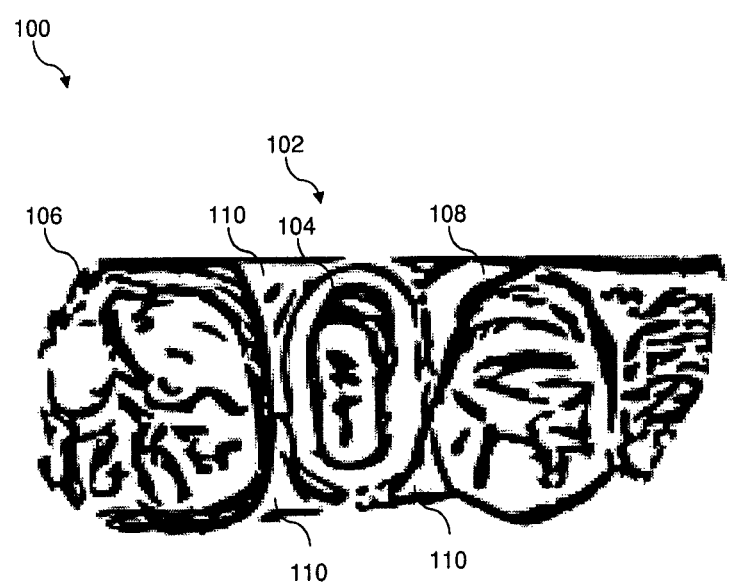
FIG. 1 is a 3D model of a prepared area of an oral cavity according to one aspect of the present disclosure.

For the purposes of promoting an understanding of the principles of the present disclosure, reference will now be made to the embodiments, or examples, illustrated in the drawings and specific language will be used to describe the same. It will nevertheless be understood that no limitation of the scope of the present disclosure is thereby intended. Any alterations and further modifications in the described embodiments, and any further applications of the principles as described herein are fully contemplated as would normally occur to one skilled in the art to which the disclosure relates.

Custom-fit prosthetics are often used in the dental field. Prosthetics are replacements for tooth and/or bone structure and include restorations, replacements, inlays, onlays, veneers, full and partial crowns, bridges, implants, posts, and the like. Typically, a dentist prepares a tooth for a restoration by removing at least a portion of the existing anatomy. The present disclosure at times refers to the prepared anatomy as a "preparation". In some instances, the resultant prepared area—including the preparation and at least a portion of the surrounding anatomy—is digitized for the purpose of designing and/or constructing a suitable prosthetic. Computer-assisted techniques are utilized to generate 3D models of the prepared area. For example, in some instances a 3D model of the preparation and surrounding anatomy (e.g., adjacent teeth, gums, etc.) is generated by a computer that processes data representing the geometries of the preparation and surrounding anatomy. The data is generated by optically scanning the prepared area and detecting or capturing the light reflected off of the preparation and surrounding features in some instances.

In that regard, laser-based systems and methods of optical scanning, such as those described in U.S. Pat. No. 7,142,312 filed Dec. 30, 2003 and titled "Laser Digitizer System for Dental Applications," U.S. Pat. No. 7,184,150 filed Mar. 19, 2004 and titled "Laser Digitizer System for Dental Applications," U.S. Pat. No. 7,355,721 filed May 5, 2004 and titled "Optical Coherence Tomography Imaging," and U.S. Pat. No. 7,342,668 filed Sep. 17, 2004 and titled "High Speed Multiple Line Three-Dimensional Digitalization," each of which is hereby incorporated by reference in its entirety, are utilized for optically scanning the prepared area in some instances. Generally, the optical scanning system includes a light source, a scanner, an image capture instrument, and a processor. In some instances, the light source produces a collimated beam of light that is projected to the scanner. The scanner redirects or scans the collimated beam of light onto the surfaces of the prepared in a desired pattern. The image capture instrument detects the light reflected from the surfaces and generates data representing a captured visual image of the scanned beam. The processor processes the data to generate the 3D model of the prepared area. In some instances, the 3D model is visualized on a computer monitor, a screen, or other display in real time as the processor generates the 3D model. In that regard, multiple images of the prepared area are obtained and processed by the processor to produce the 3D model. The images are generally captured from a plurality of positions and orientations relative to the prepared area and merged or combined to create the 3D model.

Referring now to FIG. 1, shown therein is a 3D model 100 according to one aspect of the present disclosure. In particular, the 3D model 100 of FIG. 1 illustrates a top down view of a prepared area 102. In the illustrated embodiment, the prepared area 102 includes a preparation 104, adjacent tooth structures 106 and 108, and gum areas 110. The 3D model 100 is a typical CAD-type rendering that shows the 3D detail of the prepared area but otherwise has no indication of the original textures of the surfaces that were scanned. Accordingly, there is no identifiable differentiation in the textures of the preparation 104 and surrounding gum areas 110, for example.

Figure 2:
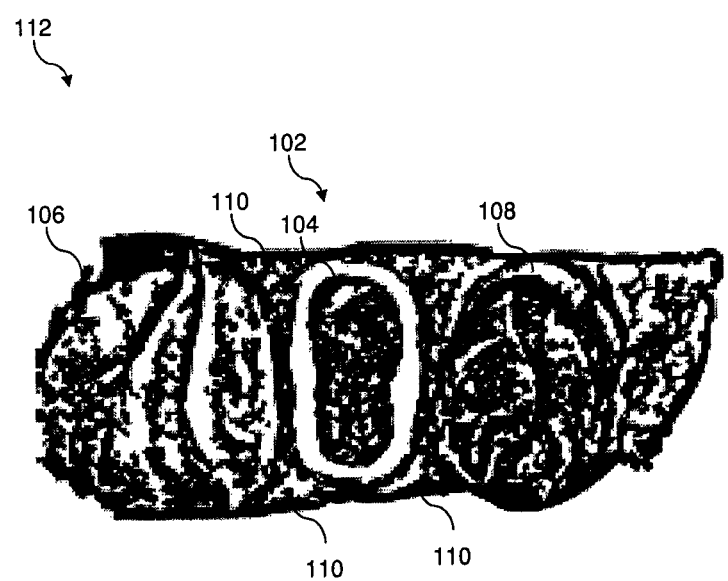
FIG. 2 is a 3D model of a prepared area of an oral cavity similar to that of FIG. 1, but having textured surfaces according to one aspect of the present disclosure.

Referring now to FIG. 2, shown therein is a 3D model 112 similar to 3D model 100 of FIG. 1, but illustrating another aspect of the present disclosure. In particular, the 3D model 112 of FIG. 2 illustrates a top down view of the prepared area 102 of FIG. 1 with textures applied to the surfaces of the preparation 104, adjacent tooth structures 106, 108, and gums 110. In that regard, the 3D model 112 overlays the actual textures of the surfaces of the preparation 104, adjacent tooth structures 106, 108, and gums 110 onto the model. So, for example, in the 3D model 112 the preparation 104 has a central portion that is much darker than the outer portion of the preparation because the central portion is composed of dental amalgam or other darker material from a previous filling or treatment, while the outer portion is composed of dental enamel. In this manner, the textures of the 3D model 112 allow the treating medical personnel to visualize and distinguish between the anatomical structures and/or materials in the prepared area 102. For example, in some instances the textures of the 3D model 112 allow the treating medical personnel to distinguish between enamel, dentin, artificial restoration materials, areas of decay, areas of discoloration, soft tissue (e.g., gums), liquids (e.g., saliva and blood) and/or other aspects of the prepared area 102. As discussed below, in some embodiments the textures or visualizations of the surfaces of the prepared area 102 are provided in monochromatic colors. In other embodiments, the textures are provided in full color. In that regard, in some instances the full color textures substantially approximate the actual colors of the various portions of the prepared area 102. It should be noted that the black-and-white line and shaded drawings of the present application do not provide the same amount of color detail or contrast available with the monochromatic or full color visualizations of the present disclosure.

Figure 3:
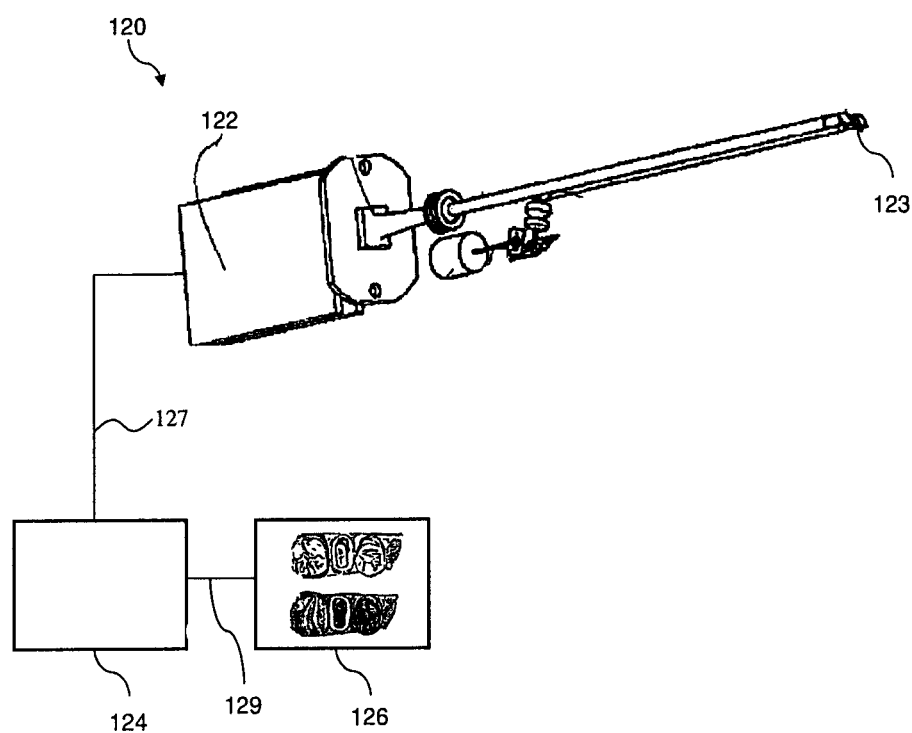
FIG. 3 is a diagrammatic schematic view of a system for generating textured 3D models according to one aspect of the present disclosure

Referring now to FIG. 3, shown therein is a system 120 for applying textures to 3D models according to one aspect of the present disclosure. In that regard, the system 120 includes a digitizer 122 for obtaining 3D coordinate data and texturing data from the prepared area. In some instances, the digitizer 122 optically scans the prepared area to obtain the 3D coordinate data and/or the texturing data. In that regard, in one embodiment the digitizer 122 generates a laser pattern that is projected on or towards the prepared area. The digitizer 122 includes a light source for generating and projecting the laser pattern from a distal end 123 of the digitizer. In some instances, the light source is a laser diode or LED that generates a laser light beam. In some embodiments, the digitizer includes collimating optics to circularize the laser light beam to generate a circular spot. The circular spot is used by the digitizer 122 to scan a pattern across the surfaces of the prepared area. In some instances, the digitizer 122 includes a scanner for scanning the laser light beam across the surfaces of the prepared area. The scanner is a 2-axis scanner in some instances. In some instances, the laser light beam is modulated at a rate between about 1 kHz and about 20 MHz, and in some instances operates at about 20 kHz. In other instances, the laser light beam is not modulated. In some instances, the digitizer 122 relays the laser pattern through relay optics such as prisms, lenses, relay rods, fiber optic cable, fiber optic bundles, and/or optical components before projecting the pattern onto the prepared area.

The digitizer 122 detects or captures the light of the laser light pattern reflected by the prepared area. The captured light is used to generate data representative of the 3D coordinates of the prepared area, which in turn is utilized to generate the 3D model. Accordingly, in some instances the digitizer includes an imaging system for detecting and/or capturing the reflected light. The reflection from the prepared area is focused onto an imaging sensor in some embodiments. Generally, the imaging sensor is a CCD sensor(s), a CMOS sensor(s), and/or other light sensitive device or array of light sensitive devices. The imaging system of the digitizer also includes the appropriate optics, such as prisms, lenses, relays, etc., for focusing the reflected light upon the image sensor. In some instances, the imaging sensor generates a digital signal representative of the reflected light captured by the imaging system. In that regard, in some instances the imaging system captures information regarding the texture of the surfaces of the prepared area in addition to the 3D coordinate data. For example, in some instances an intensity of the reflected light is captured by the imaging sensor. The intensity of the reflected light is associated with the texture of the corresponding surface. As described below with respect to FIGS. 11-13, in some instances the digitizer 122 is calibrated to account for variations in intensity introduced by the digitizer itself and/or associated hardware and software. Accordingly, in some embodiments the digital signal representative of the reflected light captured by the imaging system includes data indicative of the surface textures of the prepared area, such as intensity and/or color.

The digitizer 122 is in communication with a processing system 124 along communication connection 125. Generally, the processing system 124 includes hardware capable of executing machine readable instructions, as well as the software for executing acts (typically machine-readable instructions) to produce a desired result. Hardware generally includes at least processor-capable platforms, such as client-machines (also known as personal computers or servers), and hand-held processing devices (such as smart phones, personal digital assistants, or personal computing devices, for example). Further, hardware includes any physical device that is capable of storing machine-readable instructions, such as memory or other data storage devices. Other forms of hardware include hardware sub-systems, including communication devices such as network cards, modems, modem cards, ports, and port cards, for example. Software includes any machine code stored in any memory medium, such as RAM or ROM, and machine code stored on other devices (such as floppy disks, flash memory, CD ROM, or DVD ROM, for example). Software includes source and/or object code. In addition, software encompasses any set of instructions capable of being executed in a client machine or hand-held processing device. In some instances, the processing system 124 comprises a combination of software and hardware used for providing enhanced functionality and performance for certain embodiments of the present disclosure. One example is to directly manufacture software functions into a silicon chip. Accordingly, it should be understood that combinations of hardware and software are also included within the definition of the processing system 124 and are thus envisioned by the present disclosure as possible equivalent structures and equivalent methods. In some instances, the processing system 124 is a desktop or laptop computer.

While the processing system 124 is illustrated as a single device in FIG. 3, it is fully understood that the processing system 124 includes multiple hardware and/or software components in some instances. Further, it is understood that the processing system 124 comprises a plurality of processing systems in some instances. While the digitizer 122 is shown as being wired to the processing system 124 in FIG. 3, in other instances the digitizer is remote from the processing system 124. In that regard, the digitizer 122 communicates data to the processing system 124 wirelessly in some instances. In other instances, the digitizer 122 communicates data to the processing system 124 over a suitable communication network, such as TCP/IP, PSTN, local area network, wide area network, or otherwise. Accordingly, in some instances the processing system 124 is remote from both the digitizer 122 and the patient being treated.

The processing system 124 processes the data received from the digitizer 122 in order to generate 3D models of the prepared area. In some instances, the processing system 124 processes the data in accordance with the methods of the present disclosure in order to generate textured 3D models in addition to or in lieu of non-textured 3D models. The processing system 124 is in communication with a display device 126 for displaying the 3D models along communication connection 129. The display device 126 is generally a monitor, projector, television, or other device suitable for visually imaging the 3D models generated by the processing system 124. In some instances, the display device 126 is remote from the processing system 124. In other instances, the display device 126 is wired to the processing system 124 as shown in FIG. 3. Generally, the processing system 124 and the display device 126 are configured to display the 3D models in approximately real time as the 3D models are generated by the processing system. In some instances, the processing system 124 outputs both a textured 3D model and a corresponding non-textured 3D model, each from the same view point, to the display 126, as shown in FIG. 3.

Figure 4:
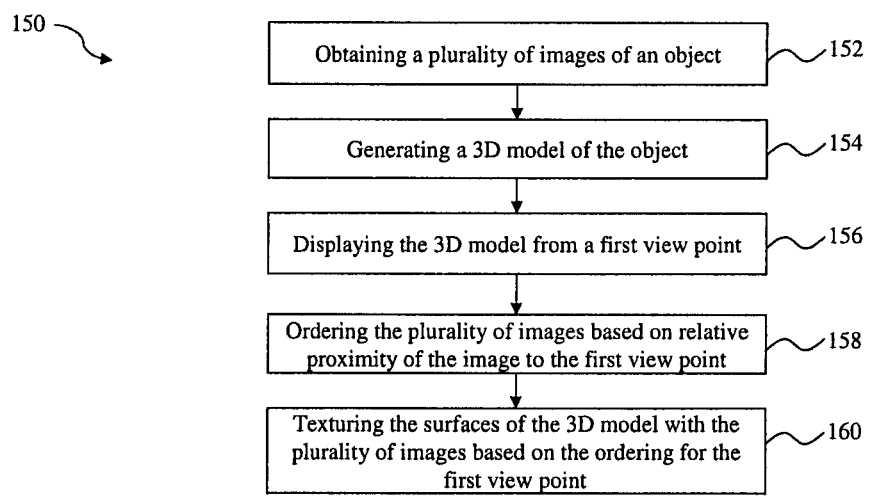
FIG. 4 is a flowchart illustrating a method of texturing a 3D model according to one aspect of the present disclosure.

Referring now to FIG. 4, shown therein is a flowchart illustrating a method 150 for applying textures to 3D models according to one aspect of the present disclosure. The method 150 begins at step 152 where a plurality of images of an object are obtained. Generally, the plurality of images are obtained at a plurality of different orientations or view points with respect to the object. In that regard, an image is associated with its particular view point in some embodiments. In some instances, the plurality of images are obtained using a 3D digitizer. In some instances, a 3D digitizer similar to those described in U.S. Pat. No. 7,142,312 filed Dec. 30, 2003 and titled "Laser Digitizer System for Dental Applications" or U.S. Pat. No. 7,184,150 filed Mar. 19, 2004 and titled "Laser Digitizer System for Dental Applications," each of which is hereby incorporated by reference in its entirety, is utilized. In that regard, in some specific instances the plurality of images are obtained simultaneously with the scanning of the object to obtain 3D coordinate data for generating the 3D model. That is, the information regarding the geometrical profile of the object and the images of object are obtained simultaneously using a 3D digitizer. In some such instances, a corresponding set of coordinate data and view point are associated with each of the plurality of images. In other instances, the information regarding the geometrical profile of the object and the images of the object are obtained separately, either using the same or different instrumentation.

The method 150 continues at step 154 where a 3D model of the object is generated. In some instances, the 3D model is generated based on information regarding the geometrical profile of the object (e.g., coordinate data). In some instances, the 3D model is generated in real time (e.g., less than about 0.1 seconds) or approximately real time based on information obtained from a 3D digitizer. In some instances, the 3D model is generated and/or updated at rate between about 60 frames per second and 1 frame per second. In some instances, the 3D model is generated and/or updated at rate of approximately 10 frames per second. In some instances, the 3D model is generated and/or updated within about 0.5 seconds or less from the time of the acquisition of 3D coordinate data. In some instances, the 3D model is generated and/or updated within about 0.1 seconds or less from the time of the acquisition of 3D coordinate data. Accordingly, in some instances the detail and completeness of the 3D model increases as more information regarding the geometrical profile of the object is obtained. Thus, in some instances the object is scanned from a plurality of view points in order to generate the 3D model. In other instances, the 3D model is generated from previous scans of the object or from other data regarding the geometrical profile of the object.

The method 150 continues at step 156 where the 3D model is displayed from a first view point. The first view point is not necessarily the initial or starting view point of the 3D model, but rather is simply intended to provide a fixed orientation of the 3D model for purposes of describing the present methodology. In that regard, in some instances a user controls the view point of the 3D model via a software interface such that the first view point is a desired view point of the user.

The method 150 continues at step 158 where the plurality of images are put in order or ranked based on the relative proximity of the image to the first view point of the 3D model. In instances where the 3D digitizer is utilized for obtaining the images, the view point of the digitizer is known for each image. Accordingly, the images are sorted based on their proximity to the first view point of 3D model. Consider the ranking of two images $T_i$ and $T_j$. $T_i$ is ranked higher or sorted above $T_j$ if the view point of $T_i$ is closer in proximity to the first view point than the view point of $T_j$. Accordingly, all of the plurality of images can be ranked or sorted using an equivalent comparison between each of the images. Accordingly, in the case of n images, the images are sorted from $T_1$ to $T_n$, where $T_1$ is the image having the view point closest in proximity to the first view point and image $T_n$ is the view point furthest in proximity to the first view point. It should be noted that the rankings of the images will change between the various view points of the 3D model. Accordingly, as discussed below the images are ordered for each view point of the 3D model.

The method 150 continues at step 160 where the surfaces of the 3D model are textured with the plurality of images based on the ordering of the images relative to the first view point. In that regard, for a particular view point the 3D model can be described as a collection B of visible triangles $B_j$, where j goes from 1 to m. Each triangle $B_j$ is a collection of three 3D coordinates $(x_{j1}, y_{j1}, z_{j1})$, $(x_{j2}, y_{j2}, z_{j2})$, and $(x_{j3}, y_{j3}, z_{j3})$, corresponding to the three corners of the triangle $B_j$. Beginning with image $T_1$, for each pixel (a, b) in $T_1$ it is determined whether the point (x, y, z) of the 3D model can be mapped using that pixel or texture of image $T_1$. In that regard, each pixel (a, b) in $T_1$ can be associated with a 3D coordinate on the object. Where the 3D digitizer is utilized this is a straightforward computation, since the image $T_1$ was taken using the digitizer from a known view point. Each 3D point (x, y, z) on the object is transformed into the camera coordinate system (x', y', z') for image $T_1$. The characteristics of the camera lens model employed by the digitizer, for example a standard pinhole camera model, are then used to transform that point (x',y',z') into an image coordinate or pixel (a, b) for $T_1$. In this manner, each pixel (a, b) in the image $T_1$ is mapped to the 3D points (x, y, z) of the 3D model. Accordingly, if the point (x, y, z) can be mapped using the particular pixel or texture of $T_1$ then every triangle containing that point is rendered with the corresponding pixels or textures of $T_1$. If the point (x, y, z) cannot be mapped using the particular pixel or texture of $T_1$ then no mapping occurs. This analysis and mapping continues for each image $T_2$ through $T_m$, where m is less than or equal to n, until all of the visible triangles $B_j$ have received a texture mapping from one of the plurality of images. In some instances each triangle receives only a single texture mapping from a single image. In that regard, in some instances multiple textures from different images are suitable for a particular triangle or 3D point of the 3D image. In such instances, the texture of the highest ranked or sorted image is utilized. Further, in order to maximize the accuracy of the 3D model and the corresponding texture mapping, the textures are not overlapped, blended, smoothed, stitched, or otherwise combined together.

In some embodiments, the images $T_1$ to $T_n$ are adjusted using intensity function prior to mapping. In that regard, in some instances the 3D digitizer includes a light source that causes uneven intensity distributions in the obtained images. Accordingly, in some instances a calibration technique is utilized to offset or correct the effects of the light source. In some instances, a new image $T_1'$ is created by taking each pixel (a, b) in $T_1$ and adjusting it using a compensation value based on the intensity function determined through calibration technique. In one example, if the closest distance from the camera to the digitizing volume is $z_0$, then a suitable compensation factor is given by $f=I(x',y',z_0)/I(x',y',z')$, where I(x, y, z) is the intensity function determined through the calibration technique. Since the intensity will tend to decrease with increased distance from the light source (according to the inverse square law), the compensation factor will be larger than 1.0. So for each pixel (a, b) in $T_1$, the intensity is determined by multiplying the compensation factor f computed above by the raw intensity value at that location (a, b) in $T_1$. Note that in general, each pixel will have a different factor f, since each pixel is mapped to a different 3D point on the 3D model that is or may be a different distance from the digitizer. Accordingly, in some embodiments the adjusted or compensated images $T_1'$ through $T_n'$ are used for the mapping. In some instances, the images are adjusted or compensated immediately upon acquisition such that the images obtained at step 152 are the compensated images.

The mapping of the textures by taking into account the intensity function and applying a compensation factor are utilized with monochromatic images in some instances. However, a similar process is used in the case of a color camera or digitizer in some instances. For example, in one embodiment the process above is performed using red illumination, green illumination, and blue illumination. In some instances, white light is utilized such that the red, green, and blue illumination are achieved at once and the corresponding intensity compensations determined without requiring separate red, green, and blue illuminations. In this case, it is possible to determine three intensity functions $I_r$, $I_g$ and $I_b$ describing the intensity behavior of the light source for each of those primary colors. Accordingly, in the case of a color digitizer where the images are color images, each pixel of the images may be represented by three intensities, namely the intensity of the red channel, the green channel, and the blue channel. The appropriate intensity compensation factor is then applied to each color channel based on the intensity function for that color. Once this process has been applied for each of the colors, the color image is adjusted or compensated. In some instances, the adjusted or compensated images are utilized for the mapping as discussed above. In the context of a wet oral environment, utilizing the different intensity functions for the different colors can be important since different wavelengths of light are absorbed and/or reflected differently by the different materials in the oral cavity.

Generally, steps 156, 158, and 160 of the method 150 are repeated each time the view point of the 3D model is changed. In some instances, the texturing of the surfaces of the 3D model is updated in real time or approximately real time as the view point of the 3D model is changed. For example, in the case of an interactive 3D graphics display, the user may change the viewpoint by means of a computer mouse or other control device, and the above analyses and mappings are rapidly performed to present the best possible texture mapping onto the 3D model in real time.

Figure 5:
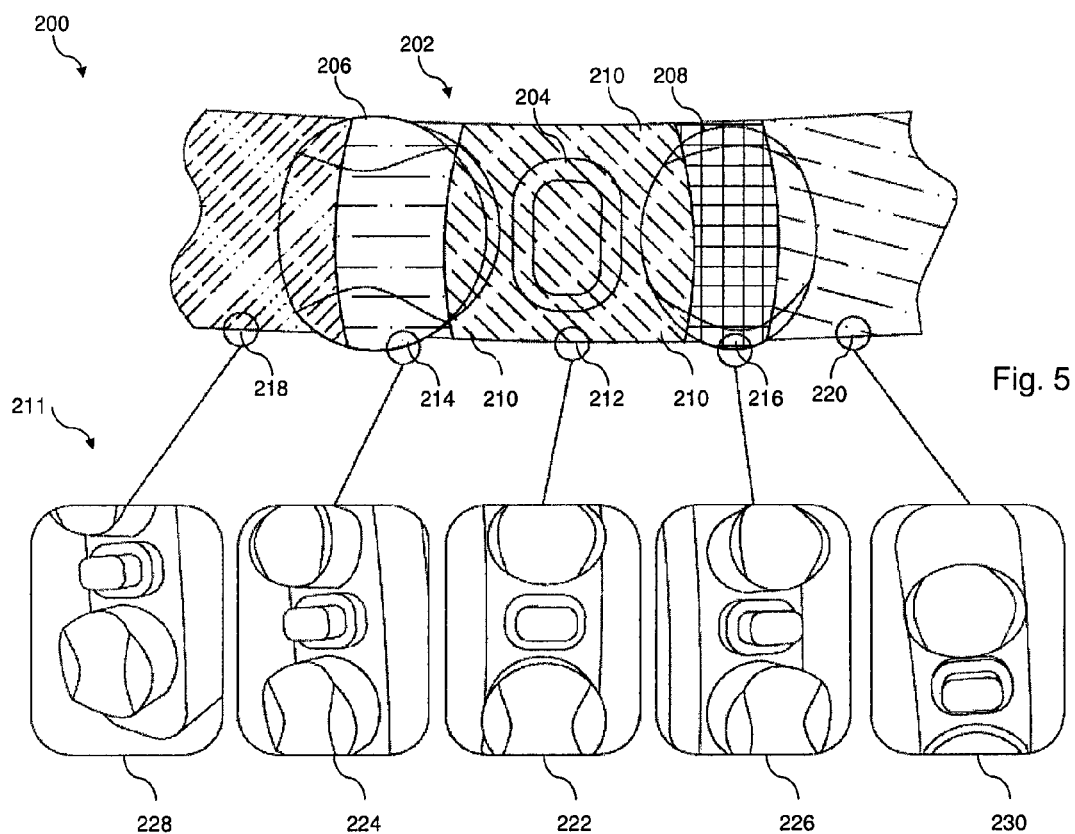
FIG. 5 is a 3D model of a prepared area of an oral cavity showing a mapping of textures from a plurality of images to the 3D model from a first view point.

Referring now to FIG. 5, shown therein is a 3D model 200 according to one aspect of the present disclosure. The textured 3D model 200 is generated utilizing the method 150 in some instances. The textured 3D model 200 includes a prepared area 204 comprising a preparation or post 204, adjacent tooth structures 206 and 208, and gum areas 210. The surfaces of the 3D model 200 are textured by the collection of images 211. In that regard, the 3D model 200 is illustrated as having five different portions 212, 214, 216, 218, and 220 that are mapped by textures from different images 222, 224, 226, 228, and 230, respectively. In that regard, the portions 212, 214, 216, 218, and 220 of the 3D model 200 are illustrated with cross-hatchings and shadings representative of the different images 222, 224, 226, 228, and 230 instead of the actual textures associated with the images to clearly show the mapping of the images to the various portions of the 3D model. As shown, each of the images 222, 224, 226, 228, and 230 is taken from a different view point. In that regard, image 222 is closest in proximity to the view point of the 3D model 200, images 224 and 226 are next closest, and images 228 and 230 are next closest. The collection of images 211 includes additional images other than images 222, 224, 226, 228, and 230 that are further away in proximity to the view point of 3D model 200 and were not utilized in texturing the 3D model 200 as shown in FIG. 5. It should be noted that the images 222, 224, 226, 228, and 230 are illustrated as black and white line drawings for simplicity sake. It is understood that in practice the images 222, 224, 226, 228, and 230 will have textures, such as shown in FIG. 2, and that the specific textures of the images are mapped to the corresponding portions of the 3D model as indicated by the cross-hatching and shading in FIG. 5.

Figure 6:
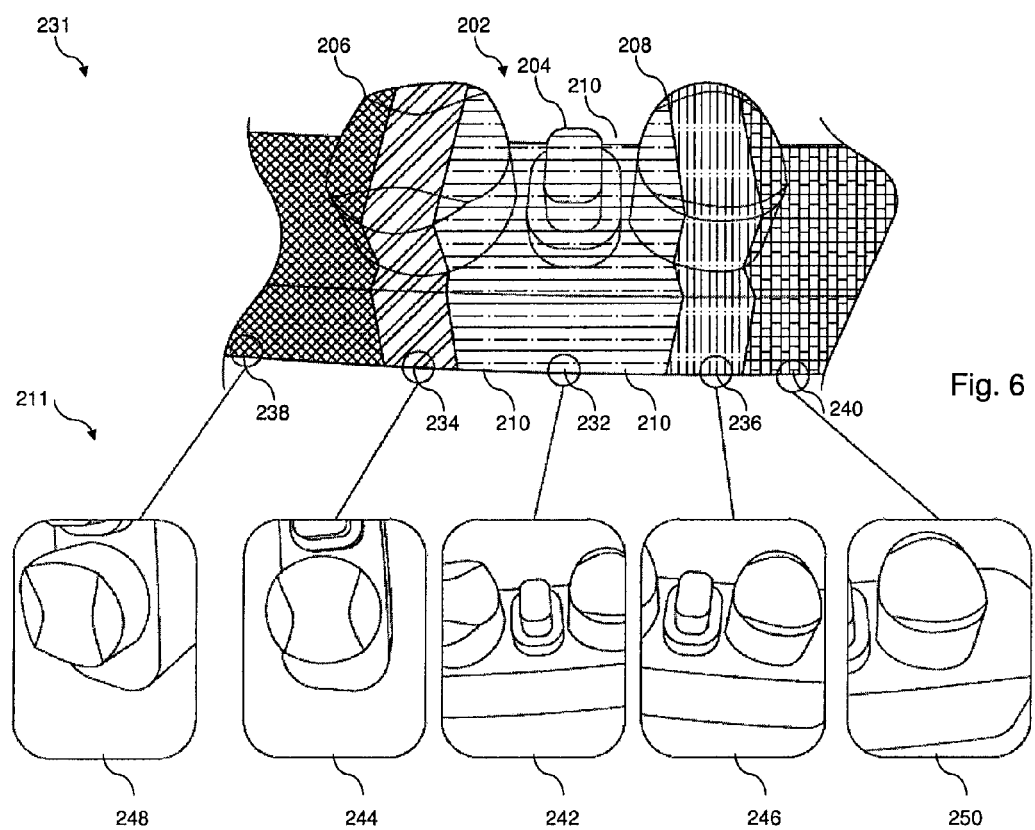
FIG. 6 is a 3D model of the prepared area of the oral cavity of FIG. 5 showing a mapping of textures from a plurality of images to the 3D model from a second alternative view point.

Referring now to FIG. 6, shown therein is a 3D model 231 similar to that of FIG. 5, but showing an alternative view point of the 3D model and corresponding alternative texture mapping of the prepared area 202. As discussed above, in some instances a user may control movement of the 3D model between the views of FIG. 5 and FIG. 6. Also as discussed above, in some instances the system and methods of the present disclosure update the texture mapping of the 3D model in real time or approximately real time as the 3D model is rotated or moved according to one aspect of the present disclosure. As shown in FIG. 6, the surfaces of the 3D model 200 are textured by the collection of images 241. The collection of images 241 is the same as collection 211 in some instances. The 3D model 231 is illustrated as having five different portions 232, 234, 236, 238, and 240 that are mapped by textures from different images 242, 244, 246, 248, and 250, respectively. Again, the portions 232, 234, 236, 238, and 240 of the 3D model 200 are illustrated with cross-hatchings and shadings representative of the different images 242, 244, 246, 248, and 250 instead of the actual textures associated with the images, such as those shown in FIG. 2, to clearly show the mapping of the images to the various portions of the 3D model. Also, each of the images 242, 244, 246, 248, and 250 is taken from a different view point. Image 242 is closest in proximity to the view point of the 3D model 231, images 244 and 246 are next closest, and images 248 and 250 are next closest. The collection of images 241 includes additional images other than images 242, 244, 246, 248, and 250 that are further away in proximity to the view point of 3D model 231 and were not utilized in texturing the 3D model 231 as shown in FIG. 6. Again, it should be noted that the images are illustrated as black and white line drawings for simplicity sake. It is understood that in practice the images will have textures similar to those of FIG. 2 and that the specific textures of the images are mapped to the corresponding portions of the 3D model as indicated by the cross-hatching and shading in FIG. 6.

It should also be noted that while the 3D models of FIGS. 5 and 6 are shown as having five bands or substantially contiguous portions each mapped by the textures of a single image, in other instances this is not the case. For example, in some instances additional or fewer numbers of images are utilized for the texturing. In some instances, the mappings are disjointed, such as where two portions of the model are mapped by textures from the same image but are separated by one or more textures from another image(s). Accordingly, it is understood that illustrated mappings are for illustration purposes only and should not be considered to be limiting in anyway. On the contrary, it is presumed that any combination of mappings of the textures from the images to the 3D model is contemplated by the present disclosure.

In the case of rendering a 3D model of an oral cavity or dental preparation, the method 150 allows vital information related to the oral cavity or dental preparation to be presented to the user with the best possible texture for the current view point. For example, during the design of a restoration on a tooth that has been prepared in the typical manner by grinding it down to form a stump or preparation the user may wish to select a 3D curve on the surface of the 3D model corresponding to the margin. In the case of a crown, the margin is the curve on the preparation that forms the externally visible interface between a subsequently designed and manufactured crown or restoration placed on the preparation. This curve is essential to the computerized design of the crown or restoration for later manufacturing by suitable a CAD/CAM system, such as those described in U.S. Pat. No. 7,226,338 filed Aug. 12, 2004 and titled "Milling Machine" and U.S. Pat. No. 7,270,592 filed Feb. 22, 2005 and titled "Milling Machine", each of which is hereby incorporated by reference in its entirety. If the interface is not manufactured correctly then the restoration will not fit properly on the preparation.

In many cases, the margin curve is determined simply by looking at a geometric aspect of an untextured 3D model (e.g., an identifiable edge of the 3D model). This is the case in some instances where the margin is above the level of the adjacent gums (supergingival). However, in many cases, the margin is at the same height as the adjacent gums (equigingival) or even below the level of the adjacent gums (subgingival). In this case, it is often not possible to determine where the margin curve is located simply by looking at the geometric aspects of an untextured 3D model as there is no discernable difference between the preparation and the gums. However, with the texturing systems and methods of the present disclosure, a user can clearly see on the textured 3D model where the margin may be located. In some instances, a user reorients the model to look at an area of particular interest. As described above, the texturing of the surfaces is updated as the model is reoriented to a new view point. The user can visually determine where the margin is by looking at the textural differences between tooth material and gum material that occurs at the margin. This textural difference is manifested as an intensity change in the case of a monochrome texture, or as a color change in the case of a color texture.

Figure 7:
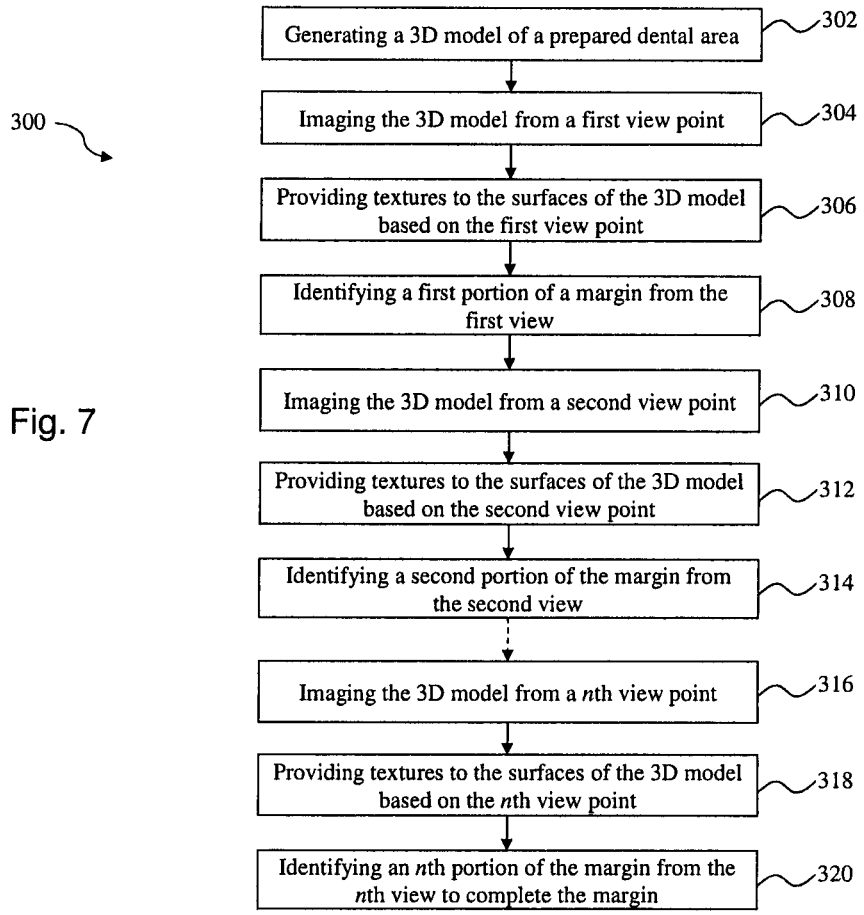
FIG. 7 is a flowchart illustrating a method of identifying a margin on a 3D model of a prepared area of an oral cavity according to one aspect of the present disclosure.
Figure 8:
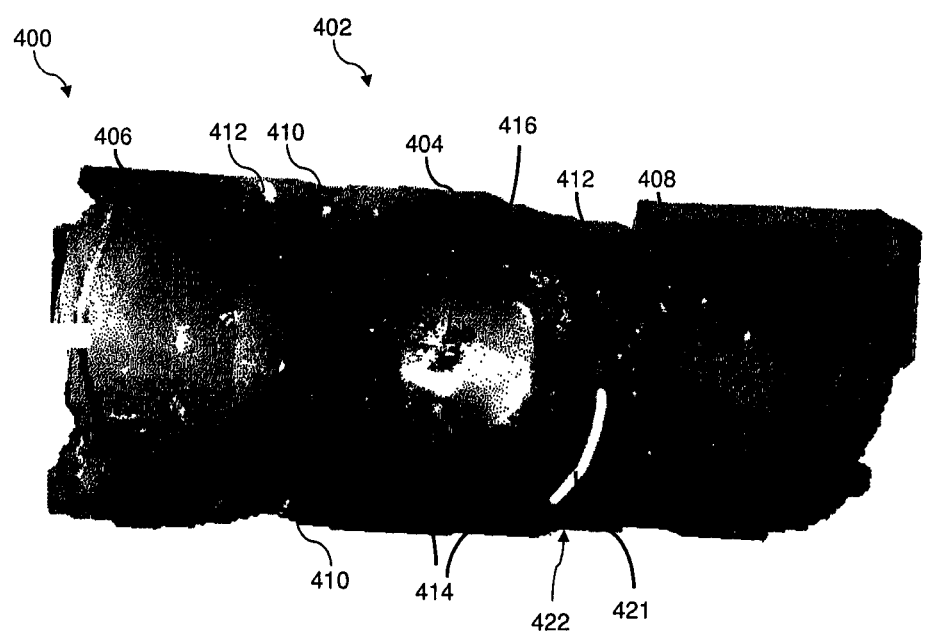
FIG. 8 is a 3D model of a prepared area of an oral cavity showing a mapping of textures from a plurality of images to the 3D model from a first view point for identifying the margin in accordance with the method of FIG. 7.

Referring now to FIG. 7, shown therein is a flowchart illustrating a method 300 for identifying and recording a margin according to one aspect of the present disclosure. The method 300 begins at step 302 where a 3D model of a prepared dental area is generated. The method 300 continues at step 304 where the 3D model is imaged or displayed from a first view point. In some instances, the first view point is selected or controlled by a user. The method 300 continues at step 306 where the surfaces of the 3D model are textured based on the first view point. Referring to FIG. 8, shown therein is a stylized textured 3D model 400 based on a first view point according to one aspect of the present disclosure. In that regard, the textured 3D model 400 includes a prepared area 402 comprising a preparation 404, adjacent tooth structures 406 and 408, and surrounding gum areas 410. In accordance with the present disclosure, the 3D model 400 is textured with the textures of particular images selected from a plurality of images of the prepared area 402. It is appreciated that some of the detail and contrast of the textures is lost in the grayscale image of FIG. 8 and that additional detail is visible in a computer generated 3D model according to the present disclosure. However, even in the view of FIG. 8 anatomical features and materials of the prepared area 402 are distinguishable. For example, FIG. 8 includes several shiny or seemingly reflective portions 412 indicative of the presence of a fluid, such as saliva. Though not shown in FIG. 8, the textured 3D models of the present disclosure distinguish between blood and saliva. As the presence of blood is indicative of a problem or potential problem in some instances, the 3D models are utilized to identify and address such problems. Also visible in the preparation 404 of FIG. 8 are a pair of screws or dental fixation members 414 from a previous dental procedure. The preparation 404 also includes an area of amalgam 416 from a previous dental procedure. The amalgam area 416 is darker than the surrounding tooth structure.

Figure 9:
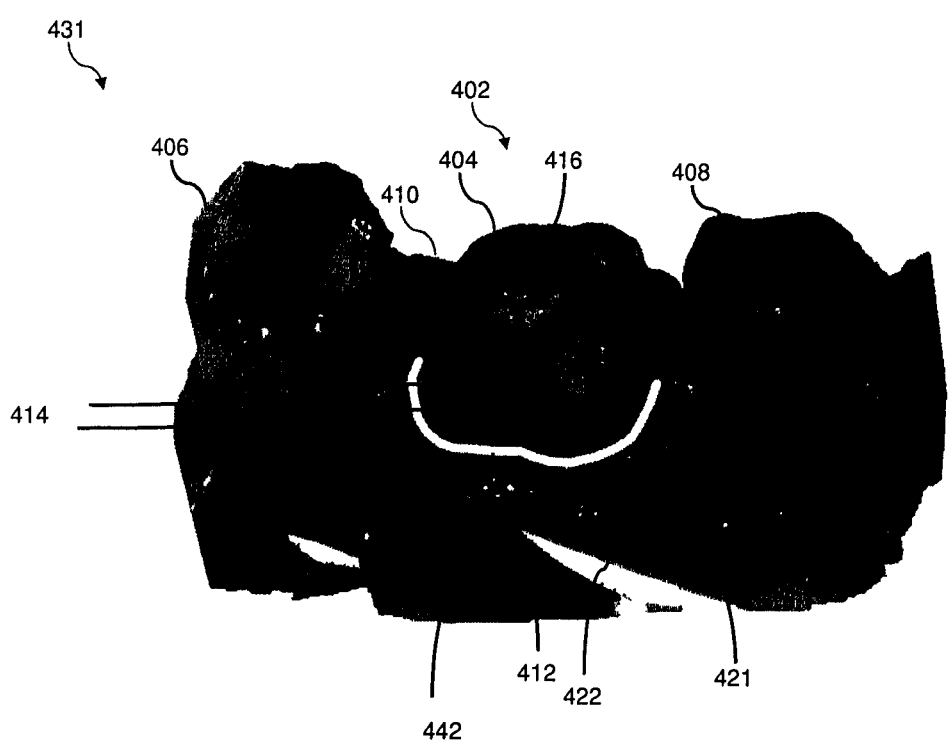
FIG. 9 is a 3D model of the prepared area of the oral cavity of FIG. 8 showing a mapping of textures from a plurality of images to the 3D model from a second alternative view point for identifying the margin in accordance with the method of FIG. 7.

Referring again to FIG. 7, the method 300 continues at step 308 where a first portion of the margin is identified from the first view. As shown in FIG. 8, in some instances a first portion 421 of a margin line 422 is marked by a user, received by the processing system, displayed on the 3D model and/or stored in memory. In some instances, the processing system generating the 3D model assists or suggests locations for the margin line based on boundaries, both structural and textural, identified in the 3D model and the user's positioning of a indicator for marking the margin line. Referring again to FIG. 7, the method 300 continues at step 310 where the 3D model is imaged or displayed from a second view point. In some instances, the second view point is selected or controlled by the user. The method 300 continues at step 312 where the surfaces of the 3D model are textured based on the second view point. Referring to FIG. 9, shown therein is a textured 3D model 431 of the prepared area 402 of FIG. 8, but showing a second view point and corresponding texturing. Referring again to FIG. 7, the method 300 continues at step 314 where a second portion of the margin is identified from the second view. As shown in FIG. 9, in some instances the second portion 442 of the margin line 422 is marked on the 3D model and/or stored in memory. In that regard, in some instances the margin line is stored as a collection of 3D coordinates defining the margin line.

Referring again to FIG. 7, the method 300 continues imaging or displaying the model from various view points, texturing the surfaces of the 3D model based on the view points, the user identifies and visually marks additional portions of the margin on the model, and the display is updated accordingly. In that regard, the 3D coordinates of the various portions of the margin are stored for retrieval in displaying the 3D model from different view points. At step 316 the 3D model is imaged from an nth view point, which is then provided with corresponding surface textures at step 318. Finally, at step 320 an nth portion of the margin line is identified to complete the margin. Subsequently the margin is utilized in some instances for milling or manufacturing a suitable crown or restoration for preparation 404. In some instances, the method 300 utilizes the systems and methods as disclosed in U.S. patent application Ser. No. 10/906,390 filed Feb. 17, 2005 and titled "Method and Computer System for Creating Dental Restoration Model", hereby incorporated by reference in its entirety, for identifying the margin line and/or creating a suitable dental restoration.

Figure 10:
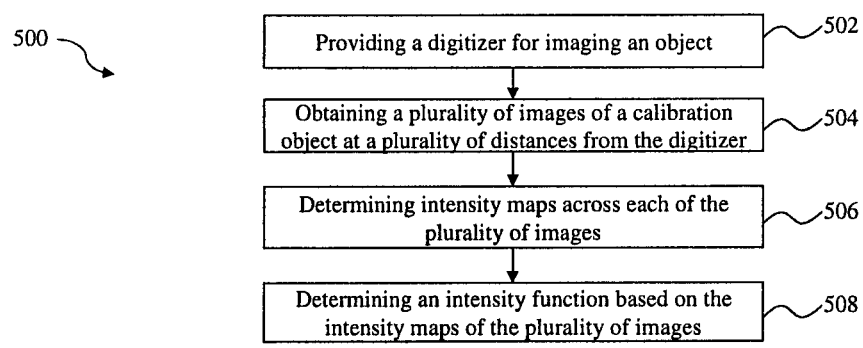
FIG. 10 is a flowchart illustrating a method of calibrating a digitizer according to one aspect of the present disclosure.

In some instances, the different lighting conditions makes realistic mapping of the different images to the 3D model impossible without adjusting the actual images themselves to accommodate for the lighting variations between each of the images. Accordingly, referring to FIG. 10, shown therein is a method 500 for calibrating a digitizer according to one aspect of the present disclosure. The method 500 begins at step 502 where a digitizer for imaging an object is provided. In some instances the method 500 is used for calibrating a 3D digitizer with a highly directional light source connected to it. In some instances, the light source used to illuminate the object is the same light source used to digitize the object. For example, in some embodiments the digitizer light source projects a sufficiently large collection of light segments onto the object so that the light segments effectively coalesce, thereby bathing the object in a full illuminated field. Generally, the method 500 is utilized to determine an intensity function that is utilized to adjust the images obtained by the digitizer to compensate for the effects of the light source.

Figure 11:
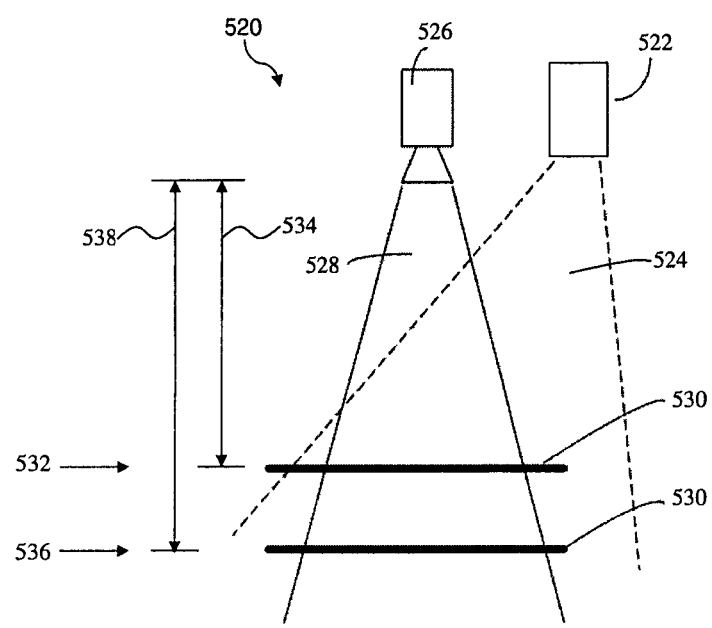
FIG. 11 is a diagrammatic schematic view of a system being calibrated in accordance with the method of FIG. 10.

The method 500 continues at step 504 where a plurality of images of a calibration object are obtained at a plurality of distances from the digitizer. In some instances, the calibration object is a planar surface. In some instances, the planar surface is of a substantially solid color. In one embodiment, the calibration object is a white planar surface. Referring to FIG. 11, shown therein is a system 520 according to one aspect of the present disclosure. In that regard, the system 520 includes a light source 522 that emits a light beam 524 and an image capture device 526 that has a digitizing volume 528. Generally, the digitizing volume is the volume of space where any visible surface of an object can be digitized or equivalently have surface 3D points or coordinates in the form (x, y, z) determined by the image capture device 526. In the present embodiment, a calibration object 530 is provided for calibrating the digitizer system 520 to accommodate for the effects of the light source 522. In that regard, in the present embodiment the calibration object 530 is a solid white planar surface. The calibration object 530 is shown as being positioned at two positions substantially perpendicular to the image capture device 526. Specifically, the calibration object 530 is shown at a first position 532, which is a distance 534 from the image capture device. In that regard, while the distance 534 is shown as being measured from the outer boundary or lens of the image capture device, it is understood that no limitation is intended thereby. Generally, the distance between the calibration object 530 and the image capture device 526 is to any suitable and/or fixed portion of the image capture device (e.g., lens, image sensor, or otherwise). The calibration object 530 is also shown at a second position 536, which is a distance 538 from the image capture device 526. The distance 538 is greater than the distance 534 of position 532.

It is understood that the calibration object is a structure having a known shape and texture (e.g., color and/or color pattern) such that the effects of light source are compensated for by identifying the differences between the observed image and the known characteristics of the calibration object. Accordingly, in some instances the calibration object comprises a substantially planar surface. In some instances, the calibration object is a 3D object having a known structural 3D profile. In some instances the calibration object has a known color pattern or color scheme. In some instances the calibration object has a substantially uniform color.

An image of the calibration object 530 is taken at each of the positions 532 and 536. In addition, images of the calibration object 530 are taken at one or more additional positions within the digitizing volume 528 of the image capture device 526 in some instances. In that regard, generally the more images of the calibration object 530 taken at different positions, the more accurate and effective the resultant calibration technique will be.

Figure 12:
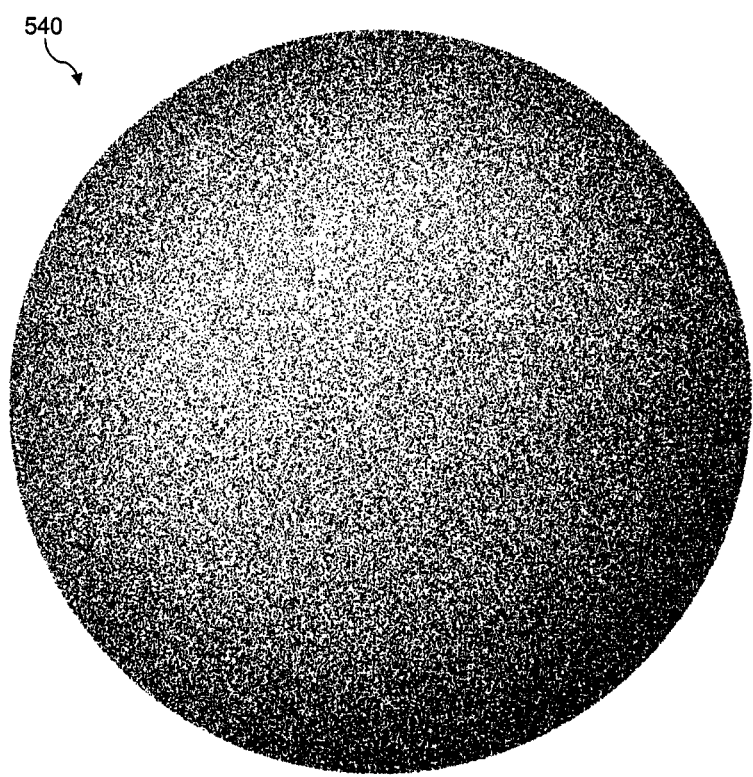
FIG. 12 is a raw image of a calibration object according to one aspect of the present disclosure.

Referring again to FIG. 10, the method 500 continues at step 506 where intensity maps for each of the plurality of images of the calibration device are determined. For each positioned or distance from the image capture device, the image is used to determine the intensity map or variation across the image field. For example, in the case of a monochromatic camera, the intensity at each point or pixel of the image is simply the pixel brightness. In the case of an 8 bit camera, this is a number between 0 and 255. For a color camera, the intensity may be computed by first converting the color image into a monochrome image or considering the intensities for different colors (e.g., red, green, and blue) separately. In that regard, for each position of the plane, an image of that plane while being illuminated by the light source 102 is taken, and recorded. Referring to FIG. 12, shown therein is an example of a image 540 of the calibration object 530 according to one aspect of the present disclosure. As shown, the image is generally darker around the edges (especially the bottom right portion of the image) and lighter in the middle (especially the left central portion of the image). However, since the calibration object 530 is a solid color object at a fixed distance from the image capture device 526 it should have a constant and uniform intensity. In some instances, the variations in intensity are attributable to the light source 522. It is understood that the intensity pattern of image 540 is exemplary and should not be considered limiting in any way. In that regard, images will have non-symmetric intensity variations in some instances. Also, in some instances the images will have non-circular profiles (e.g. rectangular or otherwise).

Referring again to FIG. 10, the method 500 continues at step 508 where an intensity function is determined based on the intensity maps of the plurality of images determined at step 506. The intensity function $I(x, y, z)$ is determined through interpolation of the intensity maps from the plurality of images of the calibration in some instances. For example, if two calibration images $A_1$ and $A_2$ of the calibration object 530 were taken at positions $z_1$ and $z_2$, respectively, then an intensity at $(x, y, z_i)$, where $z_i$ between $z_1$ and $z_2$, is estimated by linear interpolation between the intensity at $(x, y)$ in $A_1$ and $(x, y)$ in $A_2$. In this manner a general intensity function $I(x, y, z)$ can be interpolated from the plurality of images of the calibration object. Accordingly, once the calibration procedure or method 500 has been completed, for any point $(x, y, z)$ inside the digitizing volume 528 relative to the image capture device 526, the function $I(x, y, z)$ specifies the relative intensity that we expect at that point. Note that $(x, y, z)$ in this case is in the digitizer coordinate system, so that the distance z is the distance from the digitizer or the image capture device of the digitizer. The corresponding intensity function determined by method 500 is then utilized to adjust the images obtained by the digitizer to compensate for the lighting effects.

Figure 13:
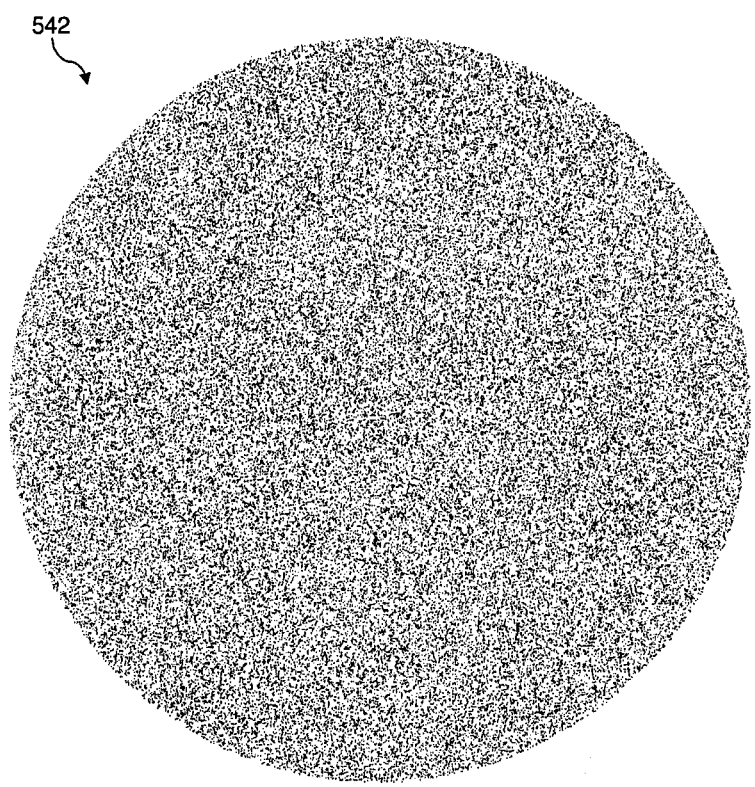
FIG. 13 is a lighting compensated version of the image of the calibration object of FIG. 12 according to one aspect of the present disclosure.

As one example, referring to FIG. 13, shown therein is an example of an adjusted image 542 of the calibration object 530 according to one aspect of the present disclosure. In that regard, the image 542 is a light-compensated or intensity-adjusted version of the image 540 of FIG. 12. As shown, the variations in intensity and/or color present in the image 540 of FIG. 12 have been substantially removed such that the image 542 has a substantially uniform color and intensity, as expected of a solid color planar surface positioned at a fixed distance from the image capture device 526. In some instances, all of the images obtained by the digitizer are calibrated upon acquisition to remove the lighting effects of the light source of the digitizer.

Generally, the intensity calibration only needs to be performed periodically. In some instances, the intensity calibration is only performed once for a given digitizer. Often the intensity calibration is performed at the time of manufacture. However, in some instances the digitizer is calibrated or recalibrated by a user. In some instances, the digitizer is calibrated before a use to ensure that the intensity functions are still accurate for the digitizer.

Figure 14:
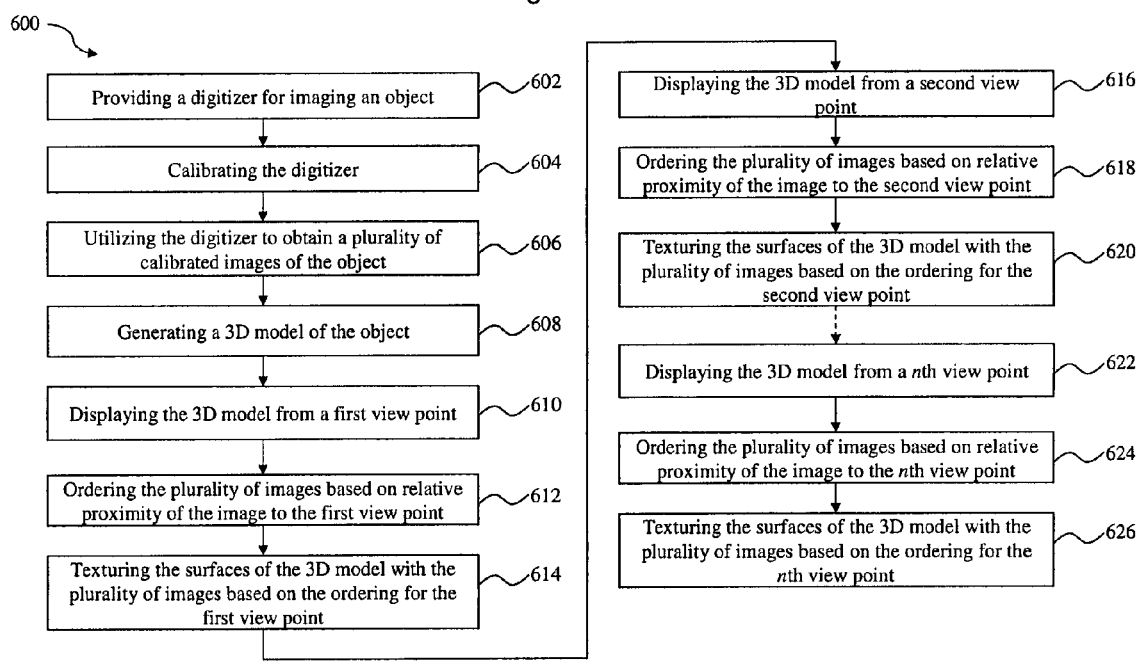
FIG. 14 a flowchart illustrating a method of providing and displaying textured 3D models according to one aspect of the present disclosure.

Referring now to FIG. 14, shown therein is a method 600 according to one aspect of the present disclosure. In some aspects, the method 600 utilizes the methods and systems described above in the present disclosure and, therefore, all aspects of the method 600 are not described in detail. The method 600 begins at step 602 where a digitizer for imaging an object is provided. In some instances the digitizer is a 3D digitizer. The digitizer includes a monochromatic imaging system in some instances. In other instances, the digitizer includes a color imaging system. The digitizer includes a light source, such as a laser or LED in some instances.

The method 600 continues at step 604 where the digitizer is calibrated. In some instances, the digitizer is calibrated to compensate or adjust the images obtained by the digitizer for lighting effects. In some instances, the digitizer includes a light source and the calibration compensates for the effects of the light source. In one embodiment, the method 500 described above is utilized to calibrate the digitizer. Where the digitizer has been previously calibrated, step 604 is omitted in some instances. The method 600 continues at step 606 where the digitizer is utilized to obtain a plurality of calibrated images of the object. In that regard, the plurality of images are obtained from a plurality of different view points in some instances. In some instances, the object is a prepared area of an oral cavity. The method 600 continues at step 608 where a 3D model of the object is generated. At step 610, the 3D model is displayed from a first view point. In some instances the first view point is selected by a user. The method 600 continues at step 612 where the plurality of images are put in order or ranked based on the relative proximity of the image to the first view point of the 3D model. The method 600 continues at step 614 where the surfaces of the 3D model are textured with the plurality of images based on the ordering of the images relative to the first view point.

At step 616, the 3D model is displayed from a second view point. In some instances the second view point is selected by a user. The method 600 continues at step 618 where the plurality of images are put in order or ranked based on the relative proximity of the image to the second view point of the 3D model. The method 600 continues at step 620 where the surfaces of the 3D model are textured with the plurality of images based on the ordering of the images relative to the second view point. Generally, the method 600 continues to display the 3D model from a plurality of view points with updated textures for each different view point. In that regard, the texturing of the surfaces of the 3D model is performed in real time as the view point of the 3D model is changed. Further, in some instances a non-textured 3D model and a textured 3D model are created simultaneously and displayed to a user (e.g., as shown on the display 126 of FIG. 3). In some instances, the non-textured 3D model is utilized by a user to ensure that a complete geometrical rendering of the subject object has been obtained, while the textured 3D model is utilized to ensure that a sufficient number of images have been obtained to generate a realistic texturing of the complete model. In this manner, in some instances both a non-textured and textured 3D model of the object are generated in real time as additional views and/or scans of the object are obtained. As described above, the view point of the 3D model is changed in some instances to assist in identifying a margin associated with a modeled dental preparation.

The method continues at step 622 where the 3D model is displayed from an nth view point. At step 624, the plurality of images are put in order or ranked based on the relative proximity of the image to the nth view point of the 3D model and, at step 626, the surfaces of the 3D model are textured based on the ordering of the images relative to the nth view point.

The present disclosure has been set forth with reference to specific exemplary embodiments and figures. It will, however, be evident that various modifications and changes may be made thereto without departing from the broader spirit and scope of the present disclosure. For example, the various components, features, or steps of the different embodiments described herein may be combined with the components, features, and steps of the other embodiments described herein. Accordingly, the specification and drawings of the present disclosure are to be regarded in an illustrative sense rather than a restrictive sense.

What is claimed is:

1. A system comprising:
a 3D digitizer comprising an attached light source and a sensor to obtain a plurality of images of an object and generate data representative of a surface of the object; and
a processing system in communication with the 3D digitizer to receive the plurality of images and the data representative of the surface of the object, the processing system generating a textured 3D model of the object from the plurality of images and the data representative of the surface of the object, where the processing system adjusts an intensity of the plurality of images using an intensity function that compensates for effects of the attached light source and maps textures from the plurality of adjusted images to corresponding points in the 3D model, each visible point in the 3D model corresponding to a texture from one of the plurality of images.

2. The system of claim 1, wherein the light source of the 3D digitizer includes a laser light source.

3. The system of claim 2, wherein the 3D digitizer is sized for intra-oral use and configured for obtaining a plurality of images of dental structures.

4. The system of claim 1, further comprising a display for displaying the textured 3D model generated by the processing system, wherein the processing system generates the textured 3D model and the display displays the textured 3D model in real time.

5. The system of claim 1, wherein the processing system determines which textures from the plurality of images to map to the corresponding points in the 3D model based on a current viewpoint of the 3D model.

6. The system of claim 5, wherein the processing system determines which textures from the plurality of images to map to the corresponding points in the 3D model by:
ordering the plurality of images based on a relative proximity of the corresponding viewpoint of the image to the current viewpoint of the 3D model,
determining which portions of the 3D model can be mapped using the image closest in proximity to the current viewpoint of the 3D model and mapping those portions of the 3D model with the corresponding textures of the image closest in proximity to the current viewpoint;
determining which portions of the 3D model can be mapped using the image next closest in proximity to the current viewpoint of the 3D model and mapping those portions of the 3D model with the corresponding textures of the image next closest in proximity to the current viewpoint until all portions of the 3D model visible from the current viewpoint are textured.

7. The system of claim 6, wherein ordering the plurality of images based on a relative proximity of the corresponding viewpoint of the image to the current viewpoint of the 3D model comprises ordering the plurality of images (1 to n) based on a relative proximity of the corresponding viewpoint of the image to the viewpoint of the 3D model, where image 1 is closest in proximity and image n is farthest in proximity to the viewpoint of the 3D model, and wherein the texture of image 1 is utilized for a primary portion of the 3D model.

8. The system of claim 7, wherein the textures of images 2 through m, where m is less than or equal to n, are utilized for secondary portions of the 3D model.

9. The system of claim 1, wherein the 3D digitizer is configured to obtain a plurality of images of a dental item.

10. A system comprising:
a digitizer configured to obtain a plurality of images of an object from a plurality of viewpoints and data representative of a three-dimensional profile of the object; and
a processing system in communication with the digitizer to receive the plurality of images and the data representative of the three-dimensional profile of the object, the processing system generating a textured three-dimensional model of the object from the plurality of images and the data representative of the three-dimensional profile of the object, wherein the processing system is configured to render the textured three-dimensional model on a display from a plurality of viewpoints, including a first viewpoint, wherein rendering the textured three-dimensional model on the display from the first viewpoint comprises mapping textures from the plurality of images to corresponding areas in the three-dimensional profile of the object to generate the textured three-dimensional model of the object, wherein mapping the textures from the plurality of images comprises:

ordering the plurality of images based on a relative proximity of the viewpoint of the image to the first viewpoint, and applying the textures to the corresponding areas in the three-dimensional profile using the images having the closest relative proximity to the first viewpoint.

11. The system of claim 10, wherein the three-dimensional profile is defined by a plurality of triangles, and wherein a texture from a single one of the plurality of images is applied to each of the plurality of triangles based on the ordering of the plurality of images to generate the textured three-dimensional model.

12. The system of claim 11, wherein if textures from multiple images are available to map to a single corresponding triangle of the 3D model, then the image having the closest proximity to the first viewpoint is utilized.

13. The system of claim 10, wherein mapping the textures from the plurality of images further comprises:
determining which portions of the three-dimensional profile can be mapped using the image in closest proximity to the first viewpoint;
mapping the portions of the three-dimensional profile that can be mapped using the image in closest proximity to the first viewpoint with a corresponding texture of the image in closest proximity;
determining which unmapped portions of the three-dimensional profile can be mapped using the image second closest in proximity to the first viewpoint;
mapping the unmapped portions of the three-dimensional profile that can be mapped using the image second closest in proximity to the first viewpoint with a corresponding texture of the image second closest in proximity.

14. The system of claim 13, wherein mapping the textures from the plurality of images further comprises:
determining which unmapped portions of the three-dimensional profile can be mapped using the image next closest in proximity to the first viewpoint;
mapping the unmapped portions of the three-dimensional profile that can be mapped using the image next closest in proximity to the first viewpoint with a corresponding texture of the image next closest in proximity until all portions of the three-dimensional profile visible from the first viewpoint are textured.

15. The system of claim 10, wherein the plurality of viewpoints includes a second viewpoint different than the first viewpoint, and wherein, for the second viewpoint, mapping the textures from the plurality of images comprises:
ordering the plurality of images based on a relative proximity of the viewpoint of the image to the second viewpoint, and
applying the textures to the corresponding areas in the three-dimensional profile using the images having the closest relative proximity to the second viewpoint.

16. A system, comprising:
a processing system configured to interface with a 3D digitizer, the processing system configured to:
receive 3D coordinate data and a plurality of images obtained by scanning a dental preparation with the 3D digitizer from a plurality of viewpoints;
generate a textured 3D model of the dental preparation from a first viewpoint for display using the 3D coordinate data and at least some of the plurality of images, where textures from the at least some of plurality of images are applied to the surfaces of the 3D model visible in the first viewpoint based on a relative proximity of the viewpoint of an image to the first viewpoint of the 3D model;
display the textured 3D model from the first viewpoint on a display in communication with the processing system;
receive an input from a user identifying a first portion of a margin on the textured 3D model from the first viewpoint;
generate the textured 3D model of the dental preparation from a second viewpoint different than the first viewpoint using the 3D coordinate data and at least some of the plurality of images, where textures from the at least some of plurality of images are applied to the surfaces of the 3D model visible in the second viewpoint based on a relative proximity of the viewpoint of an image to the second viewpoint of the 3D model;
display the textured 3D model from the second viewpoint on the display; and
receive an input from the user identifying a second portion of the margin on the textured 3D model from the second viewpoint.

17. The system of claim 16, wherein the processing system is configured to rotate the textured 3D model from the first viewpoint to the second viewpoint in response to a command input by a user.

18. The system of claim 16, wherein the processing system generates the textured 3D model from the first viewpoint by:
ranking the at least some of the plurality of images based on a relative proximity of the viewpoint of the image to the first viewpoint of the 3D model;
determining which portions of the 3D model can be mapped using the image in closest proximity to the first viewpoint;
mapping the portions of the 3D model that can be mapped using the image in closest proximity to the first viewpoint with a corresponding texture of the image in closest proximity;
determining which unmapped portions of the 3D model can be mapped using the image second closest in proximity to the first viewpoint; and
mapping the unmapped portions of the 3D model that can be mapped using the image second closest in proximity to the first viewpoint with a corresponding texture of the image second closest in proximity.

19. The method of claim 18, wherein the processing system generates the textured 3D model from the second viewpoint by:
ranking the at least some of the plurality of images based on a relative proximity of the viewpoint of the image to the second viewpoint of the 3D model;
determining which portions of the 3D model can be mapped using the image in closest proximity to the second viewpoint;
mapping the portions of the 3D model that can be mapped using the image in closest proximity to the second viewpoint with a corresponding texture of the image in closest proximity;
determining which unmapped portions of the 3D model can be mapped using the image second closest in proximity to the second viewpoint; and
mapping the unmapped portions of the 3D model that can be mapped using the image second closest in proximity to the second viewpoint with a corresponding texture of the image second closest in proximity.

* * * * *